United States Patent [19]

Auerbach et al.

[11] Patent Number: 4,637,980
[45] Date of Patent: Jan. 20, 1987

[54] EXTERNALIZATION OF PRODUCTS OF BACTERIA

[75] Inventors: Jeffrey I. Auerbach, King of Prussia; Martin Rosenberg, Malvern, both of Pa.

[73] Assignee: SmithKline Beckman Corporation, Pa.

[21] Appl. No.: 521,517

[22] Filed: Aug. 9, 1983

[51] Int. Cl.[4] ............... C07H 15/12; C12P 21/00; C12N 15/00; C12N 1/00; C12N 1/20
[52] U.S. Cl. .................... 435/68; 435/172.3; 435/172.1; 435/317; 435/253; 935/22; 935/32; 935/33; 935/38; 935/47; 536/27
[58] Field of Search ............. 435/172.3, 317, 68; 424/93; 935/22, 32, 33, 38, 47; 536/27

[56] References Cited

FOREIGN PATENT DOCUMENTS 74808 9/1981 European Pat. Off. .
61250 9/1982 European Pat. Off. .
2084584 4/1982 United Kingdom ............. 435/172.3

OTHER PUBLICATIONS

Maniatis et al, 1982, *Molecular Cloning A Laboratory Manual*, Cold Spring Harbor Laboratory, pp. 17–27.
Kleckner, 1979, (Abstract) "DNA Sequence Analysis of Tn10 Insertions: Origin and Role of 9 bp Flanking Repetions During Tn10 Translocation", Cell V 16(u) 711–20.
Rosenberg et al., Methods in Enzymology 101:123–138, (1983).
Kleckner et al., J. Mol. Biol. 116:125–159 (1977).
Remaut et al., Gene 15:81 (1981).
Sninsky et al., Gene 16:275 (1981).

*Primary Examiner*—Thomas G. Wiseman
*Assistant Examiner*—Joanne M. Giesser
*Attorney, Agent, or Firm*—Edward T. Lentz; Janice E. Williams; Alan D. Lourie

[57] ABSTRACT

A bacterial product is made by transforming a temperature sensitive lysogen with a DNA molecule which codes, directly or indirectly, for the product, culturing the transformant under permissive conditions and externalizing the product by raising the temperature to induce phage encoded functions.

31 Claims, No Drawings

EXTERNALIZATION OF PRODUCTS OF BACTERIA

FIELD OF THE INVENTION

This invention relates to genetic engineering and, in particular, to externalization of products produced by genetically engineered microorganisms.

BACKGROUND INFORMATION

A problem with using *E. coli* and other prokaryotic microorganisms as hosts for expression of desired proteins has often been externalizing the proteins from the host cells for purification. Attempts to overcome this problem include physical disruption of cells such as by homogenization or sonication, chemical disruption of cells such as by treatment with detergent or lysozyme, and fusing a DNA sequence which codes for an excretion signal peptide to a structural gene coding for the desired product. For example, Weissman et al., European Patent Application No. 61,250, disclose treatment of host cells with a lysing or permeabilizing agent; Silhavy et al., U.S. Pat. No. 4,336,336, disclose a method for fusing a gene for a cytoplasmic protein to a gene for a non-cytoplasmic protein, so that a resulting hybrid protein is transported to, near or beyond the host cell surface; Gilbert et al., U.S. Pat. No. 4,338,397, disclose a method for producing mature secreted proteins comprising inserting a structural gene for a preprotein into an expression vector.

*E. coli* can be infected by an obligatory parasite, the lambda phage, which is a double-stranded DNA virus. Lambda genetics, like *E. coli* genetics, is well-studied. See, for example, "The Bacteriophage Lambda," edit. by A. D. Hershey, Cold Spring Harbor Laboratory, New York, 1971.

Lambda, a temperate phage, multiplies in *E. coli* in either of two phases. In one, the lytic phase, the phage DNA replicates autonomously and directs formation of capsid proteins, packaging and host cell lysis. Expression of lambda DNA during the lytic phase is highly efficient. Transcription occurs on both DNA strands, on one in the rightward direction and on the other in the leftward direction. Induction can result in release of about one hundred phage particles within 50 minutes at 37° C. See, Hershey, above.

In the other phase, the lysogenic phase, lambda DNA is integrated into the host cell genome and is replicated, passively, along with the host chromosomal DNA by the host replication enzymes. A phage in the lysogenic phase is known as a prophage; the host is known as a lysogen and is said to be immune.

Immunity can be lost by occurrence of various events which induce the lytic phase. The products of the lambda int and xis genes catalyse excision of the lambda genome from the *E. coli* genome to form a covalently closed circle capable of autonomous replication. The synthesis of these genes, and either directly or indirectly, all other lambda genes is repressed by the product of the lambda cI gene. In response to certain chemicals or DNA-damaging agents, the bacteria directs synthesis of the product of the bacterial recA gene. The recA gene product proteolytically cleaves the cI repressor protein, permitting expression of the lytic phase genes. Propagation of the phage then requires interplay of several lambda regulatory elements which ultimately initiate autonomous replication of the lambda DNA. The products of the lambda P and O genes are required for DNA replication. Subsequent to DNA replication the phage must direct synthesis of viral structural proteins, that is, head and tail proteins, and their assembly into intact empty virions. Interaction of at least 18 genes is required to accomplish this. Finally, the DNA is packaged into the empty virions to produce infectious intact virions, and the cell is ruptured by endolysin, coded for by the lambda S and R genes which are activated by the product of the Q gene, thereby releasing the phages. The Q gene is activated by the N function. The N gene is repressed by the cI function.

The 18 genes required for capsid assembly lie between about map positions 3 and 36 on the rightward transcription strand, map positions being representative of percentages of total lambda DNA. The first genes, from left to right, are A, W and B; the last is J. In normal lysogens, to the right of the J gene are eight bacterial genes. Five of these, bio A, B, C, D and F, are involved in biosynthesis of biotin. A sixth, uvrB, confers resistance to ultraviolet radiation. The final two, chlA and E, confer sensitivity to chlorates. See, Guest, *Mol. Gen. Genet.* 105: 285-289 (1969) and Stevens et al, in "The Bacteriophage Lambda", ed. by Hershey, et al, cited above, at pp. 515-534.

Another lambda gene which functions in natural host cell lysis is the kil gene. The function of the kil gene is not fully understood. Cells which express the kil gene have a decreased rate of cell growth following induction. Loss of the kil function permits cells to grow at normal rates, that is, log phase growth, after induction, until lysis occurs. Like the S and R genes, the kil gene is regulated by the cI repressor, indirectly, through the N gene. See, Greer, *Virology* 66:589-604 (1975).

Temperature sensitive lysogens have been well-studied. They are described, for example, by Campbell, *Virology* 14: 22-32 (1961). The cI857 gene is a temperature sensitive cI mutant. It is functional at or below 38° C. See, Sussman et al., *C.R.H. Acad. Sci. Paris* 254:1517-1519 (1962). Similar phage systems are known to occur in other genera. For example, Lomovskaya et al., *J. Virol.* 9:258-262 (1972), report temperature sensitive mutants of a temperate phage which infects Streptomyces; Flock, *Mol. Gen. Genet.* 155: 241-247 (1977), reports temperature sensitive mutants of the temperate phage, phi-105, which infects Bacillus; Botstein et al., *Nature* 251: 584-588 (1974) report temperature sensitive mutants of the temperate phage, P22, which infects Salmonella. Jostrom et al., *J. Bacteriol.* 119:19-32 (1974), and Thompson, *J. Bacteriol.* 129:778-788 (1977), report temperature sensitive mutants of the temperate phage, phi-11, which infects Staphylococcus; Miller et al, *Virol.* 59:566-569 (1974) report temperate phages of Pseudomonas.

The lambda endolysin has been found to lyse Salmonella strains which are able to absorb the phage as reported by Botstein et al., *Ann. Rev. Genetics* 16:61-83 (1982).

Perricaudet et al., *FEBS Lett.* 56:7-11 (1975), describe deletion of lambda genes between map positions 58 and 71 (Δ 58-71) which segment includes the lambda int, xis, red, gam, cIII and kil genes.

Hershberger et al., United Kingdom Specification Application No. 2,084,584, disclose use of a lysogen as a host cell to stabilize and select for the presence of a plasmid. The authors disclose, for example, transforming a lysogen having a defective cI gene with a plasmid carrying a functional cI gene. In one disclosed embodiment, the functional cI gene is the cI857 gene.

It is known that transposable elements, that is, genes which can recombine independently of host chromosomal recombination mechanisms, can be inserted into host cells as markers. Ross et al., *Cell* 16:721-731 (1979), report physical structures of deletions and inversions promoted by the transposable tetracycline-resistance element, tn10. Davis et al., "Bacterial Genetics", Cold Spring Harbor Laboratory, New York (1980), describe uses of transposable elements.

Ruvkun et al., *Nature* 289:85-88 (1981), report integration of the transposable kanamycin resistance and neomycin resistance element, tn5, into *Rhizobium meliloti* chromosomal DNA by conjugation of a plasmid carrying tn5 followed by homologous recombination. Integration of a heterologous gene by recombination resulting from presence of homologous flanking sequences is also disclosed in European Patent Application No. 74,808.

SUMMARY OF THE INVENTION

The invention is a method of producing a product in bacteria utilizing endolysin-encoding genes from temperate phages. The method comprises transforming a temperature sensitive bacterial strain, which carries a temperature sensitive phage repressor gene and functional phage lysozyme-encoding genes such that the lysozyme-encoding genes are repressed under permissive conditions and expressed under restrictive conditions, with a DNA molecule(s) which expresses, directly or indirectly, the product; culturing the transformed strain under permissive conditions such that the product is made; raising the temperature to produce restrictive conditions; and, optionally, recovering the product from the culture medium or a concentrate thereof.

Another aspect of the invention is a method of producing a product in a bacteria which comprises transforming a bacteria which produces the product with a phage DNA sequence which carries a temperature sensitive phage repressor gene and phage lysozyme-encoding genes such that the lysozyme-encoding genes are repressed under permissive conditions and expressed under restrictive conditions, to make the bacteria lytic; culturing the transformed bacteria under permissive conditions such that the product is made; changing the temperature to provide restrictive conditions; and, optionally, recovering the product from the culture medium or a concentrate thereof.

Another aspect of the invention is a DNA fragment comprising a defective phage sequence having a temperature sensitive repressor gene and functional lysozyme-encoding genes such that the lysozyme-encoding genes are repressed under permissive conditions and expressed under restrictive conditions, a selectable marker and, preferably, flanking DNA sequences which are homologous to a contiguous sequence in the chromosome of a host cell.

Other aspects of the invention are a method of making a lytic bacteria which comprises transforming a bacteria with the DNA fragment of the invention, and bacteria comprising said DNA fragment.

Yet another aspect of the invention is a method of administering a product to a mammal comprising administering an amount of a temperature sensitive bacteria containing an effective dose of the product to the mammal, whereby the bacteria lyse within the mammal and release the product.

DETAILED DESCRIPTION OF THE INVENTION

A temperature sensitive bacteria is one which carries a prophage DNA sequence including a temperature sensitive repressor gene such that when cultured at one temperature range (permissive conditions) the repressor is functional but when cultured at another temperature range (restrictive conditions) the repressor is not functional; the repressor is not expressed or is not stable. Under restrictive conditions, the phage genes, including phage lysozyme-encoding genes, are expressed leading to cell lysis. Such temperature sensitive bacteria are lytic bacteria. Any lytic bacteria, as herein defined, can be used in the method of the invention.

Temperature sensitive temperate phage repressor genes are available or can be made by mutating such genes by procedures known to the art. By way of example, Campbell, *Virology* 14:22-32 (1961), describes a procedure for isolating temperature sensitive phage mutants. Generally, the procedure comprises mutagenizing phage-infected bacteria, such as by ultra-violet irradiation, and then incubating survivors at high temperature to cause induction of any temperature sensitive repressor mutants. The lysate is then used to infect sensitive bacteria. The new lysogens are subjected to heat induction and phage produced following the heat induction are used to prepare lysogens from sensitive bacteria. This cycling (lysogen preparation, induction, re-preparation) leads to identification of phage repressor mutants. Typically, 3 to 4 such cycles are sufficient to yield such mutants.

The description which follows relates, in large part, to lytic *E. coli* and, especially, to cI857 *E. coli* lysogens. Nevertheless, from said description persons of ordinary skill in the art will be enabled to practice the invention as it relates to other lytic *E. coli* as well as to other lytic bacteria, using repressor and endolysin-encoding genes from lambda or from other temperate phages, such as the temperate phages noted above.

cI857 lysogens, which are known and commonly available, produce cI repressor which is active at or below 38° C. but inactive above 38° C. These are preferred over other temperature sensitive *E. coli* lysogens because in addition to a mutation rendering the repressor inactive above 38° C., the cI857 gene contains a second mutation which causes the cI repressor protein to be insensitive to proteolytic cleavage by the product of the lambda recA gene. Thus, when cultured under permissive conditions, the cI repressor protein is stable and, therefore, effective in maintaining immunity.

*E. coli* strain UC5822 is a lysogen which has the cI857 mutation. It also has a point mutation in the int gene (int 6 am, an amber mutation) and in the P gene (P3 am, an amber mutation). (Amber mutations signal termination of translation). UC5822 is generally preferred over, for example, MM294(cI857) because UC5822 is defective, that is, it does not generally produce infectious phage particles. Defective lysogens are preferred, especially when used to administer a polypeptide to a mammal. UC5822, however, produces lower levels of the lysozyme, presumably because it has a lower copy number of the S and R genes, namely, one, than does MM294(cI857), namely, fifty to one hundred, after induction. Nevertheless, UC5822 lyses readily following induction.

In one aspect of the method of the invention, temperature sensitive bacteria are transformed with a DNA mmolecule(s) which codes, directly or indirectly, for a desired product. The transformation may be carried out by any technique which allows the DNA molecule to enter the host cell and to express the product. Techniques include, for example, transformation, transduction, conjugation and cell fusion. Many suitable expression vectors are well known and publicly available as are techniques for cloning genes for products and transforming cells with such molecules. Generally, the product will be a non-excreted, heterologous gene product, that is, one which is not naturally produced by the host and which is not externalized. Products which are expressed directly include polypeptides; products which are expressed indirectly include polypeptides, glycoproteins, antibiotics and other molecules such as, for example, metal ions which can be sequestered within a metallothionein-producing bacteria.

Transformed host cI857 lysogens can be grown up indefinitely under permissive conditions ($\leq 38°$ C., usually 32° to 36° C.) which are optimal for expression of the desired product. When sufficient growth has been achieved, that is, usually, when mid-log phase growth ($A_{650}=0.5$) has been achieved, synthesis of lambda endolysin is induced by culturing the lysogen under restrictive conditions. This can be accomplished by raising the temperature of the culture medium, or of a cell concentrate thereof, to, in the case of cI857, greater than 38° C., preferably 42° to 44° C., for about 90 to 120 minutes. Alternatively, the temperature of the culture medium, or of a concentrate thereof, is raised to greater than 38° C., preferably 42° to 44° C., for a shorter time, that is, a time sufficient to induce the phage DNA, preferably at least about five minutes, following which the temperature is lowered to 0° to 38° C., preferably 2° to 36° C.

Maintaining restrictive conditions for 90 to 120 minutes is preferred because lysis is more efficient and rapid. However, the latter procedure is preferred in certain applications, for example, when a desired protein is heat labile or when the cost of maintaining the restrictive conditions is prohibitive.

If the host cI857 lysogen has a functional lambda cro gene, the cells will continue to synthesize the lysozyme at any temperature at which the cells function, until lysis occurs. Although lambda endolysin is active as low as 0° C., the time needed for lysis is longer at low temperature due to a decrease in rates of protein synthesis and catalytic activity generally.

Just prior to or following induction, the cells are preferably concentrated, such as by filtration, centrifugation or other means, and incubated in this concentrated form until lysis. Such procedure facilitates collection and purification of the desired product. Following induction, the bacterial cell wall is substantially degraded. The cells, in the form of protoplasts, will continue to synthesize the desired product which is largely released into the medium through the cell membranes. Complete release into the medium is effected by lysis. Lysis is observable as a clarification of the culture medium or concentrate and/or an increase in the viscosity of the culture medium or concentrate. Lysis can be enhanced such as by mechanical agitation or rapidly changing the culturing conditions, for example, by rapidly changing temperature between 2° and 25° C. or changing the osmotic strength of the medium or concentrate. Preferably, after concentrating cells and decanting product-containing supernatant, induced cells are suspended in a minimal salts buffer or 0.1M tris buffer, 50 mM NaCl and 1 mM EDTA and agitated to effect lysis.

The desired product can then be recovered from the medium or concentrate and purified, if desirable, by known techniques.

In an alternative procedure, whole cells are concentrated and administered orally to a mammal prior to induction of the lytic phase. Induction will then occur internally, resulting in release of the desired polypeptide. This method can be especially useful for administering antigens to animals in cases in which whole cells as well as the desired antigen are preferred to provoke an immunoprotective response. For example, temperature sensitive lysogens carrying genes which code for antigens such as the LT-B antigen can be fed directly to pigs and/or calves. The amount of cells administered to each animal will be that amount which contains an effective dose. The amount of protein produced by a unit amount of cells can be calculated by known techniques.

An aspect of the invention is a DNA fragment which can be used to construct a lytic bacteria for use in the method of the invention. Such DNA fragment comprises a defective phage sequence having a temperature sensitive repressor gene and functional lysozyme-encoding genes. Such DNA fragment comprising a defective lambda sequence has a temperature sensitive cI gene and functional lambda endolysin-encoding genes (N, Q, S and R) such that the endolysin is expressed under restrictive conditions, a selectable marker, and, preferably, flanking DNA sequences which are homologous to a contiguous DNA sequence in a host cell chromosome. In one particular embodiment, the DNA fragment comprises lambda DNA which is deleted in the genes lying between map positions 58 and 71, and therefore lacks the int, xis and kil genes, has a temperature sensitive cI gene and has mutations in the O and P genes and in which the cI gene is the cI857 mutant and produces endolysin under restrictive conditions. The O and P mutations can be deletion or point mutations. Point mutations, such as the O29, P3 and P80 mutations, are preferred because they are readily available. The P3 mutation is preferred over the P80 mutation.

In another particular embodiment, the fragment comprises lambda DNA which is substantially deleted in the genes lying between map positions 3 and 71. Such fragment lacks substantially all genes essential for lambda capsid assembly as well as the int, xis and kil genes.

A host cell, *E. coli* or other bacteria, which produces a desired product, or which is previously or subsequently made to produce the desired product, such as by genetic engineering techniques, can be transformed with a phage DNA sequence which carries temperature sensitive phage repressor gene and phage lysozyme-encoding genes by known techniques. These include infecting the bacteria with a temperate phage having such temperature sensitive repressor gene, preferably a defective phage. These also include transforming the bacteria with the DNA fragment of the invention by known techniques, for example, transformation, transduction, conjugation and fusion. Transformation generally involves incorporating the fragment into a vector, such as a phage or a plasmid. For example, the fragment can be cloned into a plasmid, such as pBR322 or others, and grown up in vivo in an appropriate a host which is lacking a contiguous sequence homologous to sequences flanking the fragment or which is defective for recombination events (rec⁻). The plasmid can be recovered and used to transform an appropriate host for production of a desired product. Following transformation of such host, the fragment which has flanking DNA sequences homologous to a contiguous DNA sequence in the host chromosome will integrate by spontaneously recombining at the site of the homologous contiguous sequence. Alternatively, an appropriate host for production of a desired product can be transformed with the isolated DNA fragment in linear or circular form.

The DNA fragment carries a selection marker to facilitate selection of transformants. Selectable markers are typically genes which code for assayable enzymes, which restore prototrophy to an auxotrophic host or which confer resistance to lethal or inhibitory compounds, usually antibiotics. Preferably, the selection marker is a gene which confers antibiotic resistance as these do not require use of an auxotrophic host which may not be available or which can spontaneously revert to prototrophy. Tetracycline resistance is preferred because tetracycline is inexpensive and because resistance to tetracycline is not normally spontaneously acquired.

Presence of the marker in transformants indicates that the host comprises the DNA fragment. If the fragment integrates, the whole fragment will integrate because homology between the DNA fragment and the host cell DNA exists only in regions flanking the lambda DNA and the marker.

Absent a marker in the DNA fragment, selection of host cells carrying the lambda DNA following transduction or other transforming procedure would require super-infecting putative transductants with a defective phage (non-integrating) and selecting for immune bacterial survivors.

*E. coli* strains made lytic by integration of a DNA fragment of the invention include, for example, MG strains. These strains are lysogens in which the lambda DNA is deleted in genes lying between map positions 58 and 71, and therefore lack the int, xis, red, gam, kil and cIII genes, has the cI857 mutation and has mutations in the O and P genes and has functional N, Q, S and R genes such that endolysin is expressed under restrictive conditions. In one embodiment, strain MG1[C600 (λ Δ 58–71, cI857, P3, O29), SuII⁺, galK, lacZ, thi, gal::tn10 tet$^R$], the point (amber) mutation, is read through and the O and P genes are expressed because of the production by the host cell DNA of an amber suppressor, that is, a translational suppressor of the UAG translation termination codon.

A more preferred host cell for use in the method of the invention is one which is phenotypically O⁻ and P⁻. One embodiment, strain MG3 [N99 (λ Δ 58–71, cI857, P3, O29) galK, lacZ, thi, gal::tn10 tet$^R$], carries the same lambda DNA fragment as strain MG1. However, it is phenotypically O⁻ and P⁻ as well as tet$^R$, Δ kil, Δ int and Δ xis.

The most preferred lytic *E. coli* are MG4 strains. These are strains which are deleted in substantially all of the lambda structural protein and assembly genes and the normal right prophage-bacterial junction, that is, the right attachment site (att$^R$). In particular, they are lysogens which are deleted in substantially all lambda genes lying between map positions 3 and 71, have point mutations in the O and P genes, have a temperature sensitive cI gene and have functional N, Q, S and R genes such that endolysin is expressed under restrictive conditions, and have a selectable marker, namely, the tn10 tetracycline resistance transposable element. Such defective lysogens have 4 independent blocks to viral propagation: (i) loss of O and P replication functions, (ii) loss of att$^R$ which renders the prophage incapable of being complemented by int and xis genes from a superinfecting phage, (iii) inability to encode lambda structural genes and, (iv) the size of the lambda DNA is far below the minimum size required for packaging. These can be initially prepared by chlorate-stressing cI857, O⁻, P⁻ lysogenic strains, such as MG strains, to produce chlorate resistant mutants and selecting such mutants which are unable to complement propagation of a superinfecting heteroimmune or virulent lambda or lambdoid phage deficient in A and B functions. A DNA fragment comprising the marker, the lambda DNA and flanking sequences from the *E. coli* chromosome can be isolated from MG4 strains such as by treatment with restriction endonucleases or P1 transduction.

MG4 can be derived from MG3 by deleting all or most of the bacteriophage genes which encode the viral structural components. In order to verify the loss of these genes it is sufficient to demonstrate that the viral genome in MG4 is unable to complement and propagate a superinfecting phage which is itself defective for these genes. λ charon 3A (λ A⁻, B⁻ immφ80) is an example of a phage which can be used for this superinfection. Alternatively any phage carrying amber mutations in the A, B or other viral structural cistron can be plated on sensitive *E. coli* in the presence of a heteroimmune or virulent phage (λ vir). Recombination will occur between the two phages and lead to the formation of a recombinant, for example, λ virA⁻. The frequency of recombinants will be between 1–50%, depending on the experimental conditions. Recombinants can be recognized by their ability to plate on suppressor containing lysogens [Y mel (λ)] and their inabililty to produce plaques on non-suppressing, λ sensitive strains, such as N99. Plaques obtained from the above cross are plated onto petri dishes containing Y mel (λ) or N99 and recombinants are purified. Lambda phages deficient in A, and/or B gene function are preferred since as a consequence of their position on the lambda genome MG4 candidates which cannot complement for these functions must lack all other lambda structural genes. The use of defective phages and hosts in this way is referred to as "marker rescue" and is widely practiced, See, for example, "The Bacteriophage Lambda," edit by A. D. Hershey, Cold Spring Harbor Laboratory, 1971, especially, Stevens et al., at pp. 515–533.

The instant invention can be used to produce any product of bacteria. Examples are many and include, among others, insulin, rabies glycoprotein, K99 and 987P antigens, antibiotics, growth hormones, metallothioneins, alpha-1-antitrypsin, influenza antigens, lymphokines and interferon. In addition, the invention can be used in colony screening, RNA isolation and plasmid preparation, as the invention greatly simplifies and shortens the time needed for such procedures by bypassing the lysis step otherwise required.

In the following examples, which are illustrative of the invention and not limiting, all starting materials are readily available or can be readily prepared by techniques known in the art. Transductions were carried out substantially as described in "Experiments in Molecular Genetics", edit. by J. H. Miller, Cold Spring Harbor Laboratory, New York, (1972) pp. 201-205, which is incorporated herein by reference as though fully set forth.

EXAMPLE 1

Construction of MG0

Strain C600 (*E. coli* SuII+ K12 galI lacZ suII thi) was incubated in the presence of λ cI857 P3 O29 (gift of W. Syzbalski, U. of Wisconsin). After overnight growth at 32° C., surviving bacteria were isolated and purified. Eighty percent of these bacteria were found to be immune to superinfection, to be unable to grow at 44° C., and to produce lambda phage (following exposure to 44° C.) which were indistinguishable from λ cI857 P3 O29 (as judged by the ability of the phage to produce plaques on strain C600 but not on strain N99 (*E. coli* K12 galK lacZ suO thi). One of this class of survivors was purified and given the designation MG0 (C600 (λ cI857 P3 O29)).

EXAMPLE 2

Construction of MG0-AR6

Strain N5151 (*E. coli* K12 SA500 galK lacZ pro thr his gal8 (λ cI857 Δ 58-71 Δ H1)) was incubated in the presence of P1cm100 phage which had been grown on strain AR4 (*E. coli* K12 gal::tn10 (P1cm100)). The cross between N5151 and P1cm100 grown on AR4 resulted in the isolation of tetracycline resistant, UV sensitive, temperature sensitive lysogens. One of these isolates was purified and designated MG0-AR6 (*E. coli* K12 gal8 gal::tn10 λΔ 58-71 cI857 Δ H1(bio uvrB)).

EXAMPLE 3

Construction of MG1

MG0-AR6 was made a P1cm100 lysogen by isolating survivors of AR6 which had been incubated in the presence of P1cm100. The P1cm100 lysogen of MG0-AR6 was designated MG0-AR18.

Strain MG0 was crossed by P1 transduction with P1cm100 which had grown on MG0-AR18. After permitting time for phage absorption, the cells were subjected to a UV fluence of 4 J/m² (irradiation of 254 nm light was at a rate of 2 J/m²/s as determined by a UV dosimeter) and incubated in the presence of tetracycline. Eleven percent of tetracycline resistant colonies were resistant to UV light indicating that they did not carry the H1 deletion and thus that they possessed the lambda genes from cI through the right hand end of the phage. Specifically, this means that these clones carry the P3 and O29 mutations and intact S and R genes. One third of the UV resistant, tetracycline resistant cells were incapable of producing phage. These were therefore judged to have acquired the 58-71 deletion of lambda, and thus to have lost the int, xis and kil genes. This class was purified and designated MG1 (C600) (λΔ 58-71 cI857 P3 O29) SuII+ galK lacZ thi gal::tn10 tet$^R$).

EXAMPLE 4

Construction of MG3

MG1 was incubated in the presence of P1cm100 and survivors were purified. Among these survivors, a high percentage of MG1 cells which had become P1cm100 lysogens were identified. A P1cm100 lysogen of MG1 was purified and designated MG2.

Strain N99 was crossed by P1cm100 transduction with P1cm100 which had grown on MG2. Tetracycline resistant transductants were selected. All of these were found to be immune to lambda and were therefore judged to be lambda lysogens. One of these lysogens was purified and designated MG3 (N99 (λΔ 58-71 cI857 P3 O29)).

MG3 was determined to lyse subsequent to exposure to 44° C. for 90-120 minutes. No phage were found in cell cultures either prior to or after such exposure (<1/0.1 ml of a culture having $3.3 \times 10^8$ cells per ml). The presence of phage was assayed on C600 cells. Control cultures of *E. coli* strains which harbor non-defective lambda prophages contained between $10^5$ and $10^9$ phages per ml of a culture having $3.3 \times 10^8$ cells per ml.

EXAMPLE 5

Construction of MG3

Strain MG3 was constructed substantially as described in the above Examples except that strain N99 was lysogenized directly with λ cI857 P3 O29. The resulting lysogen was crossed by P1 transduction with strain MG0-AR18 and tetracycline resistant lysogens which lysed upon temperature induction but which did not produce phage were selected.

EXAMPLE 6

Construction of UC5822

Strain UC5822 was constructed by infecting strain N99 with λ int6 red3 cI857 P80 and λ hy5 cIimm21Δ b2. λ hy5 cIimm21 Δ b2 is a hybrid between phage λ and phage 21. The purpose of λ hy5 cIimm21 Δ b2 in this construction is to provide int function in trans which is required in order for λ int6 red3 cI857 P80 to lysogenize this strain. The Δ b2 mutation renders the Δ hy5 cIimm21 Δ b2 phage incapable of directing its own integration into this strain. A survivor of this cross which displayed immunity to superinfecting lambda but was sensitive to phage 21 was purified and designated UC5822. The strain does not survive exposure to 44° C. No phage could be detected in cultures of UC5822 either before or after incubation at 44° C.

EXAMPLE 7

Construction of MG4

Cultures of MG3 are grown in Luria broth or other complete media at 32° C. until $A_{650}=0.5$. The culture will contain approximately $5 \times 10^8$ cells/ml. The culture is then plated on Nutrient Agar plates supplemented with 0.2% glucose, and 0.2% KClO$_3$. The plates are incubated under anaerobic conditions at 32° C. until colonies form (3-5 days. Growth on this media under these conditions selects for *E. coli* which have mutations in the chl A, B, C or D gene. See, "Expts. in Molecular Genetics", J. Miller, pps 226-227.

Mutation in chlB, C or D will not lead to the isolation of MG4. Among the mutations affecting chlA expression will be point mutations in chlA and deletions extending to the left or right of chlA. Deletions extending to the left of chlA may result in disruption of the adjacent uvrB gene and thus confer a UV sensitive phenotype on the organism. For the same reason, rightward extending deletions from the chlD gene may also confer a UV sensitive phenotype on the organism. Chlorate resistant colonies obtained from the anaerobic incubation are tested to determine if they are now UV sensitive. This is conveniently done by streaking a chlorate resistant colony across a petri dish, covering ½ the dish and subjecting the other half to 10 J/m² of 254 nm UV light. This dose is sufficient to kill UV sensitive cells but not UV resistant mutants. The UV sensitive mutants (comprising mutations in chlA or chlD) are tested for the presence of the defective lambda prophage. This is done by cross streaking the cells through a streak of a homoimmune phage. Lambda sensitive bacteria are killed by the phage at the cross-streak; lambda lysogens are immune to superinfection and are not killed. As a consequence of the location of the chlA and chlD genes, the lamba genome and the uvrB gene, all UV sensitive chlD mutants will be lambda sensitive whereas some UV sensitive chlA mutants may be lambda lysogens. UV sensitive, lambda lysogens therefore contain deletions of chlA which extend leftward into uvr B. If the deletion extends through uvrB it may extend into the biotin operon and possibly into the structural lambda genes. Deletions of structural lambda genes have been obtained in this manner (Grier, Virology 66:589–604 (1975). All UV sensitive, chlA−, lambda lysogens are infected with λ virA−. After 2½ hours, the lysates are plated for λ virA− phage and for λ vir A+ recombinants. MG4 candidates which propagate λ virA− and/or produce λ virA+ phages are discarded; candidates which fail to complement λ virA− or produce virA+ carry a deletion extending from chlA through the A gene of lambda. Those MG4 candidates which possess deletions from chlA through the A gene of lambda are tested for the lytic bacteria property (lysis upon growth at >38° C.). Candidates containing the deletion which have retained the lytic bacteria property are purified as MG4.

EXAMPLE 8

Cloning in MM294(cI857) and UC5822

*E. coli* strain MM294 was incubated in the presence of λ cI857. After overnight growth at 32° C., surviving bacteria were isolated and purified. Clones which were immune to superinfection and which were unable to grow and produced phage at 44° C. were isolated. This resulting cI857 lysogenic strain, MM294 (λ cI857), and *E. coli* strain UC5822 were made competent by CaCl₂ treatment and transformed with pDN5, a plasmid carrying genes for the *E. coli* LT-B antigen and for ampicillin and tetracyline resistance.

Ampicillin and tetracycline resistant transformants of both lytic bacteria strains grew well in standard nutrient broth at 30°–32° C. and expressed LT-B antigen. The bacteria were pelleted by centrifugation and transferred to a standard nutrient broth at 42° C. Within about 90–120 minutes, cell lysis was evident and substantially complete. LT-B antigen was released into the broth. In a sample of the MM294(cI857) transformant comprising $4 \times 10^7$ cells/ml, about $2 \times 10^8$ lambda phage were collected per ml. In a similar sample of the UC5822 transformants, no phage (<20/ml were collected.

EXAMPLE 9

Cloning in UC5822

A seed culture of *E. coli* uC5822 containing the plasmid pESS2 which carries the genes for *E. coli* LT-B antigen was inoculated in a 5 ml tube of L broth containing ampicillin. After 6 hours the tube contents were transferred to 500 ml of culture medium containing ampicillin and incubated overnight with shaking at 32° C. To inoculate 10 L, 400 ml of the overnight culture was transferred to 10 L of medium containing ampicillin in a Virtis bench-top fermentor. The culture was maintained at 32° C. and each hour a 100 ml sample was monitored for growth at $A_{420}$. At 4 hours the culture was fed 200 ml of 50% dextrose and 0.1 ml of an antifoam agent. At 8 hr the culture was at 4.8 $A_{420}$ units and was shifted to 43° C. The culture was fed again at 10 hr with 200 ml of 50% dextrose, and at 14 hr the culture was stopped. A sample of a cell concentrate ("pellet") and of the cell supernatant at 4 hr, 6 hr, 8 hr, 9 hr, 10 hr, 10.6 hr and 14 hr were tested for $LT_B$ by using an ELISA test with known concentrations of $LT_B$ as standards.

The results are shown in Table I. In the first 4 to 8 hr greater than 90% of the LT-B resided in the cell, but within 2 hr after the temperature shift (10 hr after inoculation, 90% of the LT-B was in the supernatant. At 6 hr after the temperature shift, 95% of the LT-B was in the supernatant; LT-B represented 8.5% of the total protein. The yield of LT-B was far greater than the yield from *E. coli* MM294 transformed with peSS2.

Within 2–4 hours after the temperature shift lysis was evident by increased viscosity of the culture media and visible cell debris. By 4–6 hours after the temperature shift the viscosity was greatly reduced and the culture was easily pumped through an ultrafiltration apparatus to remove all debris and any remaining unlysed cells. The increased viscosity reflects release of high molecular weight DNA and RNA into the media; action of endogenous nucleases ultimately results in an observable decrease in viscosity.

TABLE I

|  | Time After Inoculation |  | $A_{420}$ | mg/ml Cell Protein | μg/ml $LT_B$ | Total $LT_B$ As Percent of Total Cell Protein |
|---|---|---|---|---|---|---|
| (Shift) (43°) | 4 | hr Pellet | 0.58 | 0.734 | 0.41 |  |
|  | 4 | hr Super |  |  | 0.06 | 0.07% |
|  | 6 | hr Pellet |  |  | 1.1 |  |
|  | 6 | hr Super | 1.8 | 1.19 | .11 | 0.1% |
|  | 8 | hr Pellet | 4.8 | 1.24 | 3.9 |  |
|  | 8 | hr Super |  |  | 0.29 | 0.3% |
|  | 10 | hr Pellet | 6.2 | 0.646 | 1.2 |  |
|  | 10 | hr Super |  |  | 14.8 | 2.5% |
|  | 10.6 | hr Pellet | 5.0 | 0.652 | 1.8 |  |
|  | 10.6 | hr Super |  |  | 39.38 | 6.3% |
|  | 14 | hr Pellet |  |  | 1.8 |  |
|  | 14 | hr Super | 4.2 | 0.652 | 53.83 | 8.5% |

EXAMPLE 10

Construction of Lytic Salmonella

An interspecies cross between Salmonella and MG3 is performed, either through conjugation or DNA transformation. Salmonella strains are normally tetracycline sensitive; MG3 is tetracycline resistant. Salmonella recombinants which have attained resistance to tetracycline are tested for their ability to grow at 42° C. Those Salmonella which lyse at this temperature have acquired, through recombination, the lytic bacteria function of MG3. This experiment is possible because (1) the lambda lytic functions are expressed in Salmonella and (2) sufficient homology exists between Salmonella and *E. coli* (MG3) to permit recombination of the *E. coli* sequences which flank the genes into Salmonella.

EXAMPLE 11

Construction of Lytic Bacillus

Method 1. The genetic elements sufficient to direct lysis of a host include the λ cI857, N, Q, S and R genes and the $P_L$ promoter. The restriction maps of these genes is known (Molecular Cloning, Maniatis et al., Cold Spring Harbor Laboratory, N.Y.). The genes are subcloned from lambda onto a plasmid (for example pBR322). A fragment of DNA from Bacillus is inserted into the plasmid at a site in a non-essential region. It is not necessary to characterize the nature or function of the host strain DNA or its orientation in the plasmid. The Bacillus is then incubated with the purified plasmid DNA, and antibiotic resistant transformants are selected. These transformants are tested to determine if they lyse after exposure to high temperature. In these transformants, the plasmid containing the lambda genes is present as an autonomously replicating unit or is integrated into the host chromosome through a recombination event between homologous Bacillus DNA on the plasmid and on the chromosome. The integration of DNA carried by plasmids which cannot replicate into the Bacillus chromosome has been described (Haldenway et al., J. Bact. 142:90-98, 1980). This method requires the expression of the lambda lytic genes in the recipient host, but does not require homology between the E. coli sequences of MG3 and the recipient bacteria.

Method 2. The phage phi-105 infects Bacillus, is temperate, and has a mutatable cI-like repressor. Derivatives of phi-105 can be made which have temperature sensitive mutations affecting this repression. Phage derivatives which lack excision or replication functions can be isolated through mutagenesis or by isolation of deletion strains. (Flock, Mol. Gen. Genet. 155:241–247, 1977). A phage derivative is obtained which possesses a thermo-labile repressor. A lysogen of this mutant is made by infecting sensitive cells with the phage at 30° C., isolating surviving cells and testing these cells for immunity to superinfecting phage and for inability to grow at 40° C. Such an organism is a phage-producing lytic bacteria. To isolate a defective lytic bacteria, the bacteria is mutagenized and surviving colonies are replica plated onto an undeveloped lawn of phi-105 sensitive Bacillus. Temperature-sensitive colonies which, following exposure to high temperature, produce few or no phage on these lawns, contain mutations affecting phage propagation. More stringent mutants may be obtained by repeating the mutagenesis. In order to mobilize this construction and easily select for transfer of this construction it is preferable to isolate a derivative which harbours an antibiotic resistance marker linked to the phi-105 genome. This can be accomplished by cloning random fragments of the Bacillus chromosome into a plasmid (which is incapable of replication in Bacillus) which carries an antibiotic resistance determinant (such as pBR322). Transformed, drug resistant cells are isolated which contain the integrated plasmid. In some of these cells the plasmid will have integrated near to the site of phi-105. The unfractionated pool of drug resistant colonies is infected with the generalized Bacillus transducing phage, pBS1. Stock of pBS1, which functions in Bacillus in exactly the same manner as Plcm100 functions in E. coli, is used to transduce Bacillus cells to drug resistance. These drug resistant transductants are tested to determine if they are thermosensitive, lytic bacteria. Approximately 1% of transductants will have acquired the lytic bacteria properties.

The preceding disclosure and examples show that the methods and compositions of matter of the invention are useful to produce and externalize products in bacteria. While the preferred embodiments of the invention are illustrated by the above, the invention is not limited to the precise constructions disclosed herein but, rather, includes all embodiments and modifications coming within the scope of the following claims.

We claim:

1. A method of producing a gene product which comprises (i) culturing a temperature sensitive bacteria, which bacteria:
   (a) expresses the gene product intracellularly,
   (b) is a lysogen defective in excision and replication functions and
   (c) contains within the prophage DNA sequence a temperature sensitive phage repressor gene and functional phage lysozyme-encoding genes, under permissive conditions such that the gene product is expressed intracellularly and the lysozyme-encoding genes are repressed and then (ii) raising the temperature to produce restrictive conditions such that the lysozyme-encoding genes are expressed.

2. The method of claim 1 wherein the temperature-sensitive phage repressor gene is a temperature sensitive lambda cI gene.

3. The method of claim 2 wherein the cI gene is the cI857 mutant.

4. The method of claim 2 wherein the bacteria is an E. coli lambda lysogen.

5. The method of claim 4 wherein the bacteria is E. coli strain UC5822.

6. The method of claim 4 wherein the lambda prophage DNA sequence is deleted in the genes lying between map positions 58 and 71 and is mutated in the O and P genes resulting in loss of O and P gene functions.

7. The method of claim 6 wherein the lambda prophage DNA sequence is flanked by a selectable marker which is a gene coding for a selectable trait and the O and P mutations are point mutations.

8. The method of claim 7 wherein the lambda prophage DNA sequence is flanked on the upstream end by the tn10 transposable tetracycline resistance element and the O and P genes are the O29 and P3 genes.

9. The method of claim 7 wherein the bacteria is an E. coli MG strain.

10. The method of claim 7 wherein the bacteria is strain MG3.

11. The method of claim 6 wherein the lambda Prophage DNA sequence is deleted in the genes lying between map positions 3 and 71.

12. The method of claim 11 wherein the lambda prophage DNA sequence is flanked by a selectable marker which is a gene coding for a selectable trait and the O and P mutations are point mutations.

13. The method of claim 12 wherein the lambda prophage DNA sequence is flanked on the upstream end by the tn10 transposable tetracycline resistance element and the O and P genes are the O29 and P3 genes.

14. The method of claim 12 wherein the bacteria is an E. coli MG4 strain.

15. A DNA fragment comprising (i) a selectable marker which is a gene coding for a selectable trait; (ii) a lambda prophage DNA sequence having a temperature sensitive cI repressor gene and functional lysozyme encoding genes such that the lysozyme-encoding genes are repressed under permissive conditions and expressed under restrictive conditions, wherein the prophage DNA sequence includes functional N, Q, S and R genes, is substantially deleted in the genes lying between map positions 58 and 71 and has mutations in the O and P genes resulting in loss of O and P gene functions; and, (iii) flanking DNA sequences homologous to a contiguous sequence in the chromosome of a host bacterial cell to permit recombination between the fragment and the host cell chromosome to occur.

16. The DNA fragment of claim 15 wherein the cI gene is the cI857 gene, the O and P mutants are the O29 and P3 mutants and the selectable marker is the tn10 transposable tetracycline resistance element.

17. The DNA fragment of claim 15 wherein the prophage DNA sequence is substantially deleted in the genes lying between map positions 3 and 71.

18. The DNA fragment of claim 17 wherein the cI gene is the cI857 gene, the O and P mutants are the O29 and P3 mutants and the selectable marker is the tn10 transposable tetracycline resistance element.

19. A bacteria comprising the DNA fragment of claim 15.

20. A bacteria comprising the DNA fragment of claim 17.

21. The bacteria of claim 19 which is an *E. coli*.

22. The bacteria of claim 20 which is an *E. coli*.

23. The bacteria of claim 21 which is an MG strain.

24. The bacteria of claim 21 which is strain MG3.

25. The bacteria of claim 22 which is strain MG4.

26. A method of making a temperature sensitive bacteria which comprises transforming a bacteria with a DNA fragment comprising (i) a selectable marker which is a gene coding for a selectable trait; (ii) a lambda prophage DNA sequence having a temperature sensitive cI repressor gene and functional lysozyme encoding genes such that the lysozyme-encoding genes are repressed under permissive conditions and expressed under restrictive conditions, wherein the prophage DNA sequence includes functional N, Q, S and R genes, is substantially deleted in the genes lying between map positions 58 and 71 and has mutations in the O and P genes resulting in loss of O and P gene functions; and, (iii) flanking DNA sequences homologous to a contiguous sequence in the chromosome of a host bacterial cell to permit recombination between the fragment and the host cell chromosome to occur.

27. The method of claim 26 wherein the cI gene is the cI857 gene, the O and P mutants are the O29 and P3 mutants and the selectable marker is the tn10 transposable tetracycline resistance element.

28. The method of claim 26 wherein the prophage DNA sequence is substantially deleted in the genes lying between map positions 3 and 71.

29. The method of claim 28 wherein the cI gene is the cI857 gene, the O and P mutants are the O29 and P3 mutants and the selectable marker is the tn10 transposable tetracycline resistance element.

30. The method of claim 26 wherein the bacteria is an *E. coli*.

31. The method of claim 28 wherein the bacteria is an *E. coli*.

* * * * *